US005558663A

United States Patent [19]
Weinberger et al.

[11] Patent Number: 5,558,663
[45] Date of Patent: Sep. 24, 1996

[54] ABSORBENT ARTICLES HAVING UNDERGARMENT COVERING COMPONENTS WITH ZONES OF EXTENSIBILITY

[75] Inventors: Eric P. Weinberger, Fairfield; Bruce W. Lavash, West Chester; Robb E. Olsen; James W. Cree, both of Cincinnati, all of Ohio

[73] Assignee: The Procter & Gamble Company, Cincinnati, Ohio

[21] Appl. No.: 277,733

[22] Filed: Jul. 20, 1994

Related U.S. Application Data

[63] Continuation-in-part of Ser. No. 915,133, Jul. 23, 1992, abandoned, Ser. No. 42,840, Apr. 5, 1993, Pat. No. 5,354,400, Ser. No. 73,256, Jun. 4, 1993, Pat. No. 5,389,094, Ser. No. 96,121, Jul. 22, 1993, Ser. No. 109,017, Aug. 18, 1993, Pat. No. 5,344,416, Ser. No. 124,180, Sep. 17, 1993, Ser. No. 192,240, Feb. 4, 1994.

[51] Int. Cl.$^6$ ..................................................... A61F 13/15
[52] U.S. Cl. ........................ 604/387; 604/385.2; 604/373
[58] Field of Search ................................ 604/373, 385.1, 604/385.2, 387

[56] References Cited

U.S. PATENT DOCUMENTS 5,344,416   9/1994   Niihari ................................... 604/387
5,389,094   2/1995   Lavash et al. ....................... 604/385.2

FOREIGN PATENT DOCUMENTS

0511905A1   11/1992   European Pat. Off. .............. 604/387

*Primary Examiner*—Robert A. H. Clarke
*Attorney, Agent, or Firm*—Jeffrey V. Bamber; Steven W. Miller; E. Kelly Linman

[57] ABSTRACT

The present invention relates to absorbent articles such as sanitary napkins, panty liners, and incontinence pads. More particularly, the present invention relates to absorbent articles, such as sanitary napkins, that have undergarment covering components (or "side wrapping elements") that automatically wrap the sides of a wearer's panties and provide an alternative to conventional side flaps. The side wrapping elements have at least one zone of extensibility and at a region therein that is stiffer than the zone of extensibility.

14 Claims, 5 Drawing Sheets

ABSORBENT ARTICLES HAVING UNDERGARMENT COVERING COMPONENTS WITH ZONES OF EXTENSIBILITY

CROSS-REFERENCE TO THE RELATED APPLICATIONS

This is a continuation-in-part of the following U.S. patent applications: Ser. No. 07/915,133 filed Jul. 23, 1992, now abandoned; Ser. No. 08/042,840 filed Apr. 5, 1993, now U.S. Pat. No. 5,354,400; Ser. No. 08/073,256 filed Jun. 4, 1993, now U.S. Pat. No. 5,389,094; Ser. No. 08/096,121 filed Jul. 22, 1993; Ser. No. 08/109,017 filed Aug. 18, 1993, now U.S. Pat. No. 5,344,416; Ser. No. 08/124,180 filed Sep. 17, 1993; and Ser. No. 08/192,240 filed Feb. 4, 1994.

FIELD OF THE INVENTION

The present invention relates to absorbent articles such as sanitary napkins, panty liners, and incontinence pads. More particularly, the present invention relates to sanitary napkins that have undergarment covering components (or "side wrapping elements") that automatically wrap the sides of a wearer's undergarments when the undergarments are pulled up, providing an alternative to conventional side flaps.

BACKGROUND OF THE INVENTION

Absorbent articles such as sanitary napkins, pantiliners, and incontinence pads are devices that are typically worn in the crotch region of an undergarment. These devices are designed to absorb and retain liquid and other discharges from the human body and to prevent body and clothing soiling. Sanitary napkins are a type of absorbent article worn by women in a pair of panties that is normally positioned between the wearer's legs, adjacent to the perineal area of the body. Sanitary napkins both with and without side flaps (or wings) are disclosed in the literature and are available in the marketplace.

Generally when sanitary napkins are provided with flaps, the flaps extend laterally from a central absorbent means and are intended to be folded around the edges of the wearer's panties in the crotch region. Commonly, the flaps are provided with an attachment means for either affixing the flaps to the underside of the wearer's panties or to the opposing flap. The flaps are particularly effective for preventing exudates from soiling the edges of the wearer's panties.

Sanitary napkins having flaps of various types are disclosed in U.S. Pat. No. 4,687,478, entitled "Shaped Sanitary Napkin With Flaps", which issued to Van Tilburg on Aug. 18, 1987; U.S. Pat. No. 4,608,04, entitled "Sanitary Napkin Attachment Means", which issued to Mattingly on Aug. 26, 1986; U.S. Pat. No. 4,589,876, entitled "Sanitary Napkin", which issued to Van Tilburg on May 20, 1986 and its Reexamination Pat. No. B1 4,589,876, Certificate of Reexamination issued Apr. 27, 1993; U.S. Pat. No. 4,285,343, entitled "Sanitary Napkin", which issued to McNair on Aug. 25, 1981; U.S. Pat. No. 3,397,697, entitled "Disposable Sanitary Shield For Undergarments", which issued to Rickard on Aug. 20, 1968; and, U.S. Pat. No. 2,787,271, entitled "Sanitary Napkin", which issued to Clark on Apr. 2, 1957.

While sanitary napkins having flaps are commonly viewed as providing better protection against soiling as compared to sanitary napkins without flaps, some women find applying sanitary napkins having flaps to be inconvenient for various reasons. For instance, some women find it to be difficult to attach the flaps to the underside of the crotch of their panties. This can be due to factors such as the tendency for the adhesive fasteners on the flaps to stick to themselves or to other parts of the sanitary napkin. As a result, some women still prefer a sanitary napkin without flaps. In addition, some women who generally prefer a sanitary napkin with flaps, occasionally (such as during periods of light flow) prefer a sanitary napkin without flaps. Therefore, there is a need for a sanitary napkin which provides an alternative to sanitary napkins having conventional side flaps while still providing the protection of side flaps.

Several variations of sanitary napkins having conventional flaps that attempt to solve some, but not all of these problems are disclosed in the patent literature. For example, U.S. Pat. No. 4,911,701 issued to Mavinkurve discloses a sanitary napkin having elastic strands for providing a greater convex shape to the body-facing portion of the central absorbent and for enabling adhesive-free placement of the flaps of a winged napkin embodiment into a pair of panties. The sanitary napkin described in the Mavinkurve patent, however, still appears to require the user to manipulate the flaps (by first flipping the flaps upward and then placing the flaps in her panties and flipping the flaps back down) since the flaps appear to be pre-disposed to be in a downward folded condition. The Mavinkurve patent also requires that individual elastic strands be attached in a contracted condition to the central absorbent portion of the napkin and/or to its wings or flaps. The napkins described in the Mavinkurve patent can, therefore, be difficult and expensive to manufacture. U.S. Pat. No. 4,940,462 issued to Salerno discloses a sanitary napkin with longitudinally expandable flaps. The flaps are designed to fold over the exterior of the wearer's panty and then to expand to conform with the contour of the panties. The Salerno patent, however, appears to require conventional adhesive fasteners to retain the flaps in place on the underside of the wearer's panties.

Thus, a need exists for an absorbent article, such as a sanitary napkin, that is provided with an alternative to conventional flaps. In particular, a need exists for a sanitary napkin having an alternative to conventional flaps which provides the protection from soiling of conventional flaps and which can conveniently and efficiently solve the problems caused when attempting to attach conventional flaps to the underside of the wearer's panties.

It is, therefore, an object of the present invention to provide an absorbent article, such as a sanitary napkin, that is able to provide coverage to the wearer's panties to reduce side soiling (i.e., staining of the edges of the panty crotch) without the use of conventional flaps.

It is another object of the present invention to provide an absorbent article, such as a sanitary napkin, that automatically wraps around the sides of the wearer's panties by the simple action of the wearer pulling up her panties.

It is still another object of the present invention to provide an absorbent article, such as a sanitary napkin, that is able to wrap around the sides of the wearer's panties and stay without providing flaps having panty fasteners thereon, and without attaching separate elastic strands to the sanitary napkin.

These and other objects of the present invention will be more readily apparent when considered in reference to the following description and when taken in conjunction with the accompanying drawings.

SUMMARY OF THE INVENTION

The present invention provides an absorbent article, such as a sanitary napkin. The sanitary napkin of the present invention has a pair of undergarment covering components (or "side wrapping elements") that provide coverage to the wearer's panties to reduce side soiling (i.e., staining of the edges of the panty crotch) without the use of conventional flaps.

The sanitary napkin comprises a main body portion comprising a liquid previous topsheet, a liquid impervious backsheet joined to the topsheet, and an absorbent core positioned between the topsheet and the backsheet. The side wrapping elements are preferably joined to the garment-facing side of the main body portion inboard of the longitudinal side edges of the main body portion. The side wrapping elements comprise a pair of flexible elements that extend a short distance beyond the crotch edge portions of the wearer's undergarment. The side wrapping elements are preferably each provided with at least one zone of extensibility, preferably two spaced apart zones of extensibility. The zones of extensibility are regions of the side wrapping elements that have a greater range of extension than the adjacent regions of the side wrapping elements. The side wrapping elements preferably comprise at least one zone of extensibility on each side of the transverse centerline of the side wrapping elements and a stiffer, less extensible intermediate region along the transverse centerline of the side wrapping elements.

The side wrapping elements have improved resistance to bending, crumpling, and other types of transverse deformation than a similar side wrapping element would have if it were made of the same material and was provided with extensibility along its full length. The stiffer, less extensible intermediate region located along the transverse centerline of the side wrapping elements provides the side wrapping elements with the improved resistance to bending and crumpling. The improved resistance to bending and crumpling ensures that the side wrapping elements will fold over the elasticated sides of the wearer's panties, and will not crumple when the wearer's thighs apply compressive forces on the distal edges of the side wrapping elements. The fact that the side wrapping elements have crumpling resistance and zones of extensibility allows the side wrapping elements to automatically fold around the crotch edge portions of the wearer's undergarment toward the underside of the undergarment and to remain so folded over the crotch edge when the absorbent article is placed in an undergarment and the undergarment is pulled up adjacent the wearer's body. The zones of extensibility and stiffer intermediate region, thus, provide a mechanism for controlling the manner and location of folding of the side wrapping elements.

The sanitary napkin of the present invention provides an alternative to sanitary napkins having conventional side flaps for several reasons. The side wrapping elements do not extend far enough outward beyond the side edges of the wearer's panties to cause any inconvenience to the wearer. The side wrapping elements require no action on the part of the wearer to fold the side wrapping elements under her panties or to attach the same to her panties. The side wrapping elements stay in place well enough to cover the sides edges of the wearer's panties without affixing them underneath the wearer's panties.

In an alternative embodiment, however, the sanitary napkin may be provided with a fastener, such as a pressure sensitive adhesive, for additional security. The adhesive fastener may be provided on the garment-facing side of the main body portion and also extend onto the garment-facing side of the side wrapping elements. In this embodiment, particularly in narrow panty crotches, the side wrapping elements may fold around the side edge of the wearer's panty crotch so that portions of the side wrapping elements overlap and, due to the placement of the pressure sensitive adhesive, the portions of each side wrapping element adhere to each other at a location outboard of the side edges of the undergarment. This forms a novel structure that pinches the side edge of the panties between the folded portion of the side wrapping elements.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

1. General Characteristics of the Absorbent Article

Figures 1, 2:
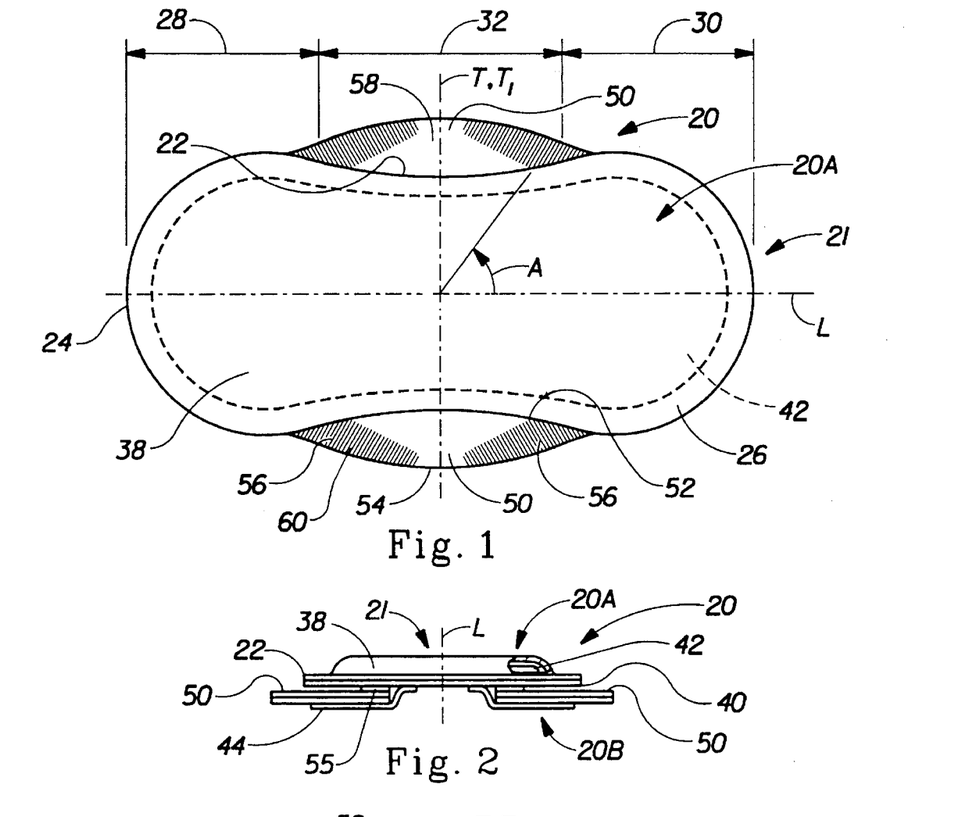
FIG. 1 is a top plan view of the sanitary napkin of the present invention.
FIG. 2 is an end view of the sanitary napkin shown in FIG. 1 shown with a portion of the topsheet cut away to show the absorbent core.
Figure 3:
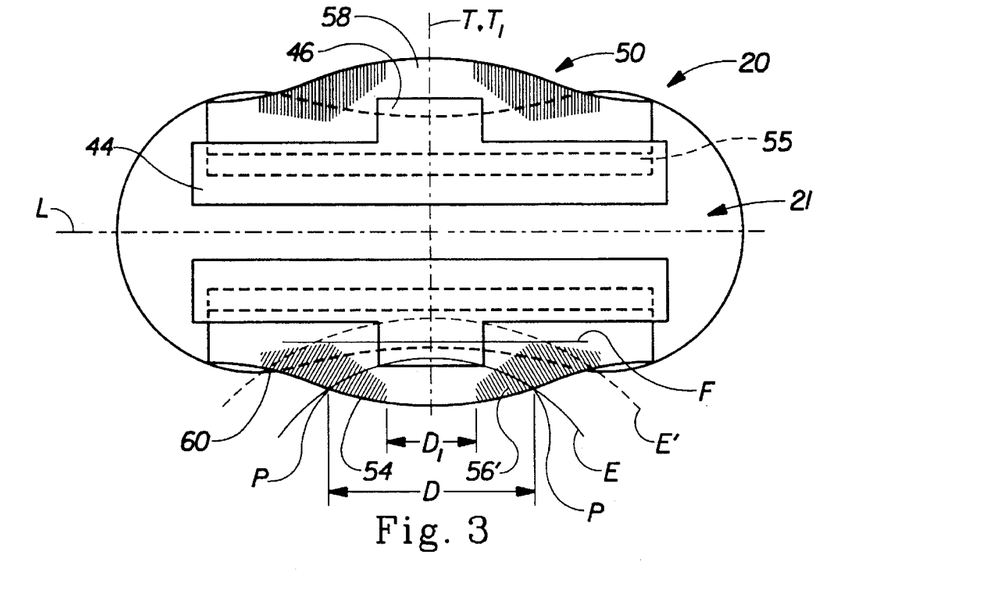
FIG. 3 is a slightly modified bottom plan view of the sanitary napkin shown in FIG.

FIGS. 1–3 show one preferred embodiment of a disposable absorbent article of the present invention 20. The present invention relates to absorbent articles, such as sanitary napkins. More particularly, the present invention relates to sanitary napkins that have a main body portion 21 and a pair of side wrapping elements 50 that automatically wrap the sides of the wearer's panties when the wearer places the sanitary napkin in her panties and pulls her panties up.

The sanitary napkin 20 has two surfaces, a liquid pervious body-contacting surface or "body surface" 20A and a liquid impervious garment surface 20B. The sanitary napkin 20 is shown in FIG. 1 as viewed from its body surface 20A. The body surface 20A is intended to be worn adjacent to the body of the wearer. The garment surface 20B of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline L and a transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction.

FIG. 1 shows that the main body portion 21 of the sanitary napkin 20 comprises the portion of the sanitary napkin without the side wrapping elements. The main body portion 21 has two spaced apart longitudinal edges 22, two spaced apart transverse or end edges (or "ends") 24, which together form the periphery 26 of the main body portion. The main body portion also has two end regions, which are designated first end region 28 and second end region 30. A central region 32 is disposed between the end regions 28 and 30. The end regions 28 and 30 extend outwardly from the edges of the central region 32 about 1/8 to about 1/3 of the length of the main body portion. A detailed description of a sanitary napkin having a central region 32 and the two end regions 28 and 30 is contained in U.S. Pat. No. 4,690,680 issued to Higgins on Sept. 1, 1987.

The main body portion 21 of the sanitary napkin 20 can be of any thickness, including relatively thick, relatively thin, or even very thin. The embodiment of the sanitary napkin 20 shown in FIGS. 1–3 of the drawings is intended to be an example of a relatively thin sanitary napkin, preferably an "ultra-thin" sanitary napkin. It should be understood, however, when viewing these figures the number of layers of material shown cause the sanitary napkin 20 to appear much thicker than it actually is. An "ultra-thin" sanitary napkin 20 as described in U.S. Pat. No. 4,950,264 and 5,009,653 issued to Osborn preferably has a caliper of less than about 3 millimeters. The sanitary napkin 20 shown should preferably also be relatively flexible, so that it is comfortable for the wearer. It should be understood that the sanitary napkin shown is merely one preferred embodiment, and that is not limited to absorbent articles of the type or having the specific configurations shown in the drawings.

FIG. 2 shows the individual components of the main body portion 21 of the sanitary napkin 20 of the present invention. The main body portion 21 of the sanitary napkin generally comprises at least three primary components. These include a liquid pervious topsheet 38, a liquid impervious backsheet 40, and an absorbent core 42 positioned between the topsheet 38 and the backsheet 40. There are also occasions, however, when one or more of these components, such as the backsheet, can be replaced by a component that serves as part of the side wrapping elements 50 described below. The topsheet, the backsheet, and the absorbent core may be assembled in a variety of configurations known in the art (including so called "sandwich" products and "tube" products).

Several preferred sanitary napkin configurations are described generally in U.S. Pat. 4,321,924, "Bordered Disposable Absorbent Article" issued to Ahr on Mar. 30, 1982; U.S. Pat. No. 4,425,130, "Compound Sanitary Napkin" issued to DesMarais on Jan. 10, 1984; U.S. Pat. No. 4,950,264, "Thin, Flexible Sanitary Napkin" issued to Osborn on Aug. 21, 1990; U.S. Pat. No. 5,308,346, "Elasticized Sanitary Napkin" issued to Sneller, et al. on May 3, 1994; U.S. patent application Ser. No. 08/096,121 entitled "Absorbent Articles Having Panty Covering Components That Naturally Wrap the Sides of Panties" filed Jul. 22, 1993, in the name of Lavash, et al.; and U.S. patent application Ser. No. 08/124,180 entitled "Absorbent Articles Having Panty Covering Components Comprising Extensible Web Materials Which Exhibit Elastic-Like Behavior" filed Sep. 17, 1993, in the name of Mansfield, et al. The main body portion 21 of the sanitary napkin may also be comprised of one or more extensible components such as those sanitary napkins, and the like described in U.S. patent application Ser. Nos. 07/915,133 and 07/915,284 both filed Jul. 23, 1992, in the name of Osborn, et al. (PCT Publication Nos. WO 93/01785 and 93/01786 both published Feb. 4, 1993).

FIGS. 1–3 show a preferred embodiment of the sanitary napkin 20 assembled in a sandwich construction in which the topsheet 38 and the backsheet 40 have length and width dimensions generally larger than those of the absorbent core 42. The topsheet 38 and the backsheet 40 extend beyond the edges of the absorbent core 42 to thereby form portions of the periphery 26. The sanitary napkin 20 of the present invention comprises pair of side wrapping elements 50 that extend laterally outward beyond the longitudinal side edges 22 of the main body portion 21 from their proximal edges 52 to their distal edges 54.

The side wrapping elements 50 can be of any suitable size and shape. The distal edges 54 of the side wrapping elements preferably extend outward beyond the longitudinal side edges 22 of the main body portion 21, a distance of less than one-half the width of the main body portion. The side wrapping elements 50 of the present invention may have any of the dimensions and characteristics set forth for the panty covering components in the aforementioned U.S. patent application Ser. Nos. 08/096,121 and 08/124,180 filed in the names of Lavash, et al. and Mansfield, et al., which are incorporated by reference herein.

The side wrapping elements 50 can, as shown in FIGS. 1–3, comprise two separate components that are joined to the garment-facing side of the main body portion 21. The side wrapping elements 50 are otherwise unattached to the garment-facing side of the main body portion 21 of the sanitary napkin 20 between the points of attachment and the longitudinal side edges 22 of the main body portion. The side wrapping elements 50 can be joined to the garment-facing side of the main body portion 21 by any suitable attachment mechanism. Suitable attachment mechanisms include, but are not limited to adhesives, and the like. In the embodiment shown, strips of adhesive 55 are used for this purpose.

The side wrapping elements 50 can, however, be joined to the main body portion 21 in any suitable manner. The term "joined", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. Thus, the side wrapping elements 50 can be integral extensions of the topsheet 38 and backsheet 40 of the main body portion 21. In other embodiments, instead of comprising two separate components, the side wrapping elements 50 can comprise a single component (which may be referred to as a "panty covering component" or "undergarment covering component"). In still other embodiments, each side wrapping element 50 can comprise more than one component.

In the preferred embodiment shown in FIGS. 1–3, the side wrapping elements 50 each comprise a web of material having at least one, and preferably two zones of extensibility 56 therein. The zones of extensibility 56 can be primarily extensible in the longitudinal direction (that is, they are extensible more in the longitudinal direction than in the transverse direction). In other embodiments, the zones of extensibility 56 can be primarily extensible in the transverse direction, or in any direction between the longitudinal direction and the transverse direction. The side wrapping element 50 shown at the top of FIG. 3 has zones of extensibility that are primarily extensible in the longitudinal direction. The remaining zones of extensibility 56 in the embodiment shown in FIGS. 1–3 are extensible in a direction that is between the longitudinal direction and the transverse direction. The extensibility of all the zones of extensibility 56 on the side wrapping elements 50 can be in the same direction. Alternatively, one or more of the zones of extensibility 56 may be extensible in a different direction.

The zones of extensibility 56 are preferably capable of extending between about 20% and about 80%, more preferably between about 40% and about 70%, and most preferably between about 60% and about 70% under the forces associated with wearing the sanitary napkin in a pair of panties. Preferably, the zones of extensibility 56 are capable of such extension under forces of less than about 100–200 grams$_f$ per inch (about 40–80 gf/cm), more preferably under forces of less than about 50 grams$_f$ per inch (about 20 gf/cm). The zones of extensibility 56 are also preferably extensible without being elasticized or elasticated (where separate elastic bands are stretched and attached to the side wrapping elements 50 in an extensible condition). Further, any inherent elasticity in the zones of extensibility 56 (that is, any tendency of the material comprising the zones of extensibility to return to its original dimension) is generally relatively low to non-existent.

FIG. 3 shows the preferred locations for the zones of extensibility 56 and the manner in which the preferred amounts of extensibility in these locations are determined. The curved line, E, in FIG. 3 represents the location where the edges of a wearer's panty crotch might lie when the sanitary napkin 20 is placed in a pair of panties prior to the side wrapping elements 50 being folded around the edges of the panties. The panty edges E cross the distal edge 54 of the side wrapping element 50 at two points, designated P. The zones of extensibility 56 should be located where the panty edges E cross the distal edges 54 of the side wrapping elements 50. The distance, D, between these two points P varies depending on the size and style of panties. A representative distance D is equal to about 85 mm. FIG. 3 also shows portions 56' of the zones of extensibility that are disposed longitudinally inboard of the points P (that is, toward the transverse centerline $T_1$ of the side wrapping elements). In order to fit a wide variety of panty sizes and styles, it is preferred that each of the portions 56' of the zones of extensibility between points P is capable of extending greater than or equal to about 10–15 mm and that the combined extensibility in these portions for each side wrapping element is greater than or equal to about 20–30 mm. The longitudinal distance between the points within zones of extensibility 56 that are on opposite sides of the transverse centerline of a side wrapping element 50 is preferably between about 20 mm and about 150 mm, and more preferably is between about 30–130 mm, and most preferably between about 30–100 mm.

The side wrapping elements 50, as shown in FIG. 3, preferably also have a trapezoidally-shaped intermediate region or zone 58 located between the zones of extensibility 56. The intermediate region 58 comprises a portion of the distal edges 54 of the side wrapping elements. This intermediate region 58 is stiffer (that is, more resistant to bending) than the zones of extensibility 56. The intermediate region 58 can also be less extensible than the portions of the side wrapping elements that comprise the zones of extensibility 56. The intermediate region 58 provides the side wrapping elements 50 with greater resistance to bending and crumpling so that the side wrapping elements will fold over the panty elastic, rather than crumple, when they are subject to compression by the wearer's thighs. The stiffer intermediate region 58 also helps to maintain panty elastic coverage when the wearer pulls her panties down to check the sanitary napkin for soiling, and then pulls her panties back up. The stiffer material ensures that the side wrapping elements do not fold upward over top of the main body portion, and stay on the same plane as the main body portion of the sanitary napkin, where flimsier material would be pushed upward during the motion associated with pulling the panties downward and might tend to fold upward over the topsheet when the panties are pulled back up. Upon pulling the panty and sanitary napkin back up, flimsier material may also not be caught by the wearer's thighs and go back into place. The intermediate region 58 preferably has a distal edge portion that forms a portion of the distal edge 54 of the side wrapping elements. The length $D_1$ shown in FIG. 3 of the distal edge portion, is preferably at least about 20 mm, and more preferably about 30 min.

The side wrapping elements 50 can be made from any of the materials used in the construction of the main body portion 21 of the sanitary napkin. The side wrapping elements 50 in the embodiment shown in FIGS. 1–3 preferably comprise a laminate of three materials, a soft extensible coverstock material such as a longitudinally extensible spunbond nonwoven web or a soft extensible formed film, an extensible intermediate layer such as a three dimensional formed film, and an extensible liquid impervious backing such as a polyethylene film backsheet material.

The coverstock material preferably comprises a spunbonded polyethylene nonwoven web having a basis weight of between about 15 gsm and 60 gsm The nonwoven web is made of single fiber filaments that are typically between about 1 inch and 4 inches (about 2.5 cm to about 10 cm) long which have a denier ranging between about 1 Dpf and about 6.5 Dpf. Each of the filaments possesses its own extensibility ranging from about 5% to about 200% per filament. The nonwoven web is preferably point bonded with a total bonded area of between about 6% and about 40%. The nonwoven web is capable of extension in the longitudinal direction of between about 10% and about 200% under forces ranging from about 40 g/in at 10% elongation to about 550 g/in at 200% elongation without breaking. Suitable nonwoven webs include a product known as Spunbond PE, which was obtained from Polybond, Incorporated of Waynesboro, Va. and a product known as COROLIND PE, which was obtained from Corovin GMBH of Germany.

The extensible intermediate layer preferably comprises a variation of a three dimensional formed film known as DRI-WEAVE which is used as a topsheet on sanitary napkins manufactured by the Procter & Gamble Company, Cincinnati, Ohio under U.S. Pat. Nos. 4,342,314 issued to Radel, et al. and 4,463,045 issued to Ahr, et al. The three dimensional film has an embossed thickness of between about 15 mils to about 35 mils (about 0.38 mm to about 0.89 mm) and is not apertured all the way through as in the case of DRI-WEAVE topsheet material, but is formed so that the apertures are closed off on the side of the film that would ordinarily face away from the wearer's body in use. The formed film resin composition is modified by adding a blend of linear low density polyethylene ("LLDPE") and high density polyethylene ("HDPE") such that the formed film is capable of extending between about 60% and about 200% in the longitudinal direction. The formed film is preferably extrusion coated onto the nonwoven web.

The polyethylene backsheet material is a film comprised of LLDPE that preferably has a caliper of between about 0.4–1.5 mil, more preferably about 1 mil. A preferred polyethylene film is known as P18–1401 and is obtained from Clopay Corporation of Cincinnati, Ohio. This polyethylene film can either be glued to the formed film side of the laminate of the nonwoven and formed film such as by a spiral application of adhesives, or it can be extruded thereon.

The composite laminate preferably has a caliper of between about 5–60 mil (about 0.13–1.5 mm) and is capable of extending between about 25–70% without tearing under forces of between about 50–200 grams/in (about 20–80 gf/cm). This particular laminate is chosen to provide a soft body-contacting surface, good extensibility in the zones of extensibility when the zones of extensibility are formed therein, good resistance to folding and crumpling and a liquid impervious barrier. This laminate is believed to be unique for several reasons. It is believed to be unique because it contains a drawable, but non-elastomeric coverstock. Coverstock materials are often non-extensible. If a coverstock material is extensible, however, it is generally provided with an elastic or elastomeric type of extensibility. The spunbonded nonwoven coverstock used in the laminate described herein differs from such conventional materials because after extension, it tends to return less than 10% toward its unextended dimension. The intermediate formed film layer provides the laminate with some substantiality and loft (thickness) without negating the overall extensibility of the laminate. The laminate described herein is particularly useful in cases where it is desirable to make a material extensible without prior stretching and bonding of elastic strands to another material.

This laminate is also particularly useful where it is desirable to perform further mechanical operations on a material to provide the entire material with extensibility or to provide zones of greater extensibility in selected regions of the material. Such further mechanical operations include situations where the material is to be subjected to the "SELFing" process described in U.S. patent application Ser. No. 08/124,180, or if it is ring rolled as described below. The laminate is particularly well suited for such mechanical processing because the components of the laminate, such as the drawable fibers of the nonwoven are less resistant to such mechanical manipulation and, thus, tends to better retain its mechanically induced characteristics since it has little, if any, tendency to retract to its previous unaltered state.

(It should also be understood that the laminate described herein is useful in any application where the above properties are desired. This can include not only use of the laminate in the side wrapping elements of the present invention but it also includes usage of the laminate as one of the component parts of other types of disposable absorbent articles such as diapers and training pants. Examples of diapers and training pants are described in U.S. Pat. No. 5,151,092 issued to Buell and U.S. Pat. No. 5,246,433 issued to Hasse, et al., respectively.)

The side wrapping elements 50 can be provided with zones of extensibility 56 in a non-limiting number of different manners. The side wrapping elements 50 may, for example, comprise a substantially inextensible material that is provided with extensible regions for the zones of extensibility. The extensible regions can be created in any suitable manner, including but not limited to mechanically straining, corrugating, "ring rolling", heating and deforming, subjecting portions of the side wrapping elements 50 to compression between mating plates, and the like.

In other embodiments, the different regions of the side wrapping elements can be provided by forming the side wrapping elements out of materials having different extensibilities. For example, the side wrapping elements 50 can be comprised of a laminate of an extensible material and an inextensible material. In such an embodiment, the inextensible material can be provided in the configuration of the side wrapping elements. The inextensible material can have holes cut out where the zones of extensibility are to be located. This inextensible material can then be laminated to the extensible material to form a side wrapping element with zones of extensibility where the holes were cut from the inextensible material.

The embodiment shown in FIGS. 1–3 has zones of extensibility 56 formed by ring rolling (or pre-corrugating) two regions of the side wrapping elements. Suitable methods for ring rolling are described in U.S. Pat. No. 4,107,364 issued to Sisson on Aug. 15, 1978, U.S. Pat. No. 4,834,741 issued to Sabee on May 30, 1989, U.S. Pat. No. 5,143,679 issued to Gerald M. Weber, et al. on Sept. 1, 1992, U.S. Pat. No. 5,156,793 issued to Kenneth B. Buell, et al. on Oct. 20, 1992, and U.S. Pat. No. 5,167,897 issued to Gerald M. Weber, et al. on December 1, 1992.

The side wrapping elements 50 in most of the views of the embodiment shown in FIGS. 1–3 are provided with ring rolled corrugations having fold lines 60 that are angled away from the longitudinal centerline L. The fold lines 60 can form any angle with the longitudinal centerline, between greater than 0° and less than or equal to 180°. The fold lines 60 in most of the views of the embodiment shown in FIGS. 1–3 form an angle of between about 40°–45° with the longitudinal centerline L. The upper portion of FIG. 3, as noted above, shows that in alternative embodiments, the ring rolling can be applied so that the fold lines 60 in the corrugations are oriented generally in the transverse direction to provide zones of extensibility 56 that are primarily extensible in the longitudinal direction.

The configuration and location of the zones of extensibility 56 in the embodiment shown in FIGS. 1–3 is preferred for several reasons. The fact that the zones of extensibility 56 are spaced apart and separated by the stiffened intermediate region 58 provides improved resistance to bending and crumpling and more control over the manner of folding around the edges of the wearer's panties. The side wrapping elements 50 will typically fold in the zones of extensibility 56 and the intermediate region 58 between the points where the panty edges cross the distal edges 54 of the side wrapping elements 50. This makes the side wrapping elements sturdier and capable of more reliable folding than if the side wrapping elements were made entirely extensible and/or were made of materials having the same stiffness over their entire area.

Another reason the zones of extensibility shown in FIGS. 1–3 are preferred is seen when panties having a narrow crotch are worn. If the wearer is wearing panties that have such a narrow crotch width that their edges lie inboard of the zones of extensibility as shown by the dashed line E', the side wrapping elements 50 will be predisposed to fold along a fold line, F, that connects the innermost points of the zones of extensibility 56. The zones of extensibility 56, thus, allow the sanitary napkin to fit a wide variety of panty sizes.

Preferably, the lateral distance between the innermost points of the zones of extensibility on the opposed side wrapping elements is about 75 mm. The rest of the dimensions for the sanitary napkin or features thereof can be scaled from FIGS. 1 and 3 using the 75 mm dimension provided above.

The garment surface 20B of the sanitary napkin 20 may include, and preferably does include, fasteners for attaching the sanitary napkin to the wearer's undergarment. FIG. 3 shows the central pad fastener 44 which is adapted to secure the portion of the sanitary napkin underlying the main body portion 21 to the crotch region of an undergarment. Any types of fasteners known in the art can be used. Fasteners comprising adhesives have been found to work well for this purpose, with pressure-sensitive adhesives being preferred. Before the sanitary napkin 20 is placed in use, if an adhesive fastener is used, the adhesive is typically covered with a removable cover strip or release liner in order to keep the adhesive from sticking to a surface other than the crotch portion of the panty prior to use. Suitable release liners are described in the U.S. Pat. No. 4,917,697.

Figure 4:
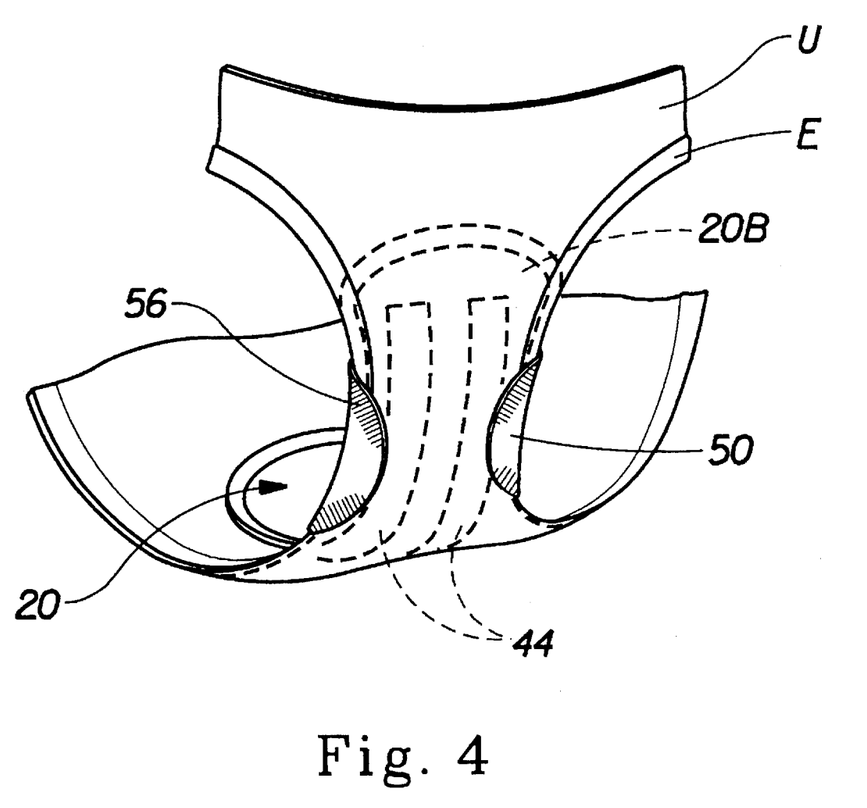
FIG. 4 is a perspective view of a portion of a panty with the sanitary napkin of the present invention in place with the side wrapping elements at an angle with the underside of the wearer's panties.

FIG. 3 shows a preferred arrangement which utilizes a pair of spaced apart longitudinally-oriented strips or zones of adhesive that are centered about the longitudinal centerline L. Each of the longitudinally-oriented zones of adhesive has a central lateral extension 46. The central lateral extensions 46 serve to adhere the side wrapping elements 50 around the elasticated edges of the crotch portion of the wearer's undergarments during vigorous motions by the wearer (although such fasteners are generally not required under normal circumstances). The central lateral extensions 46 of fastener adhesive can serve to secure the side wrapping elements 50 to the top of the wearer's panties, and/or to the underside of the wearer's panties as shown in FIG. 4. In the preferred embodiment, the central lateral extensions 46 are spaced between greater than about 65 mm and less than about 90 mm apart so that they can be secured directly over and/or under the elasticized side edges of the wearer's panties when the sanitary napkin is centered in the wearer's panties. The central lateral extensions 46 are preferably located in the stiffer intermediate regions 58 of the side wrapping elements 50. The central lateral extensions 46 are preferably contiguous with the longitudinally-oriented zones of adhesive, although this is not required. The presence of the intermediate region 58 provides an advantage in constructing embodiments that are provided with such central lateral extensions of adhesive. Since there is no need to provide the intermediate region 58 with extensibility, it is typically not corrugated so that it is easier to apply an adhesive-type fastener to the garment-facing side of the intermediate region 58.

Figure 4A:
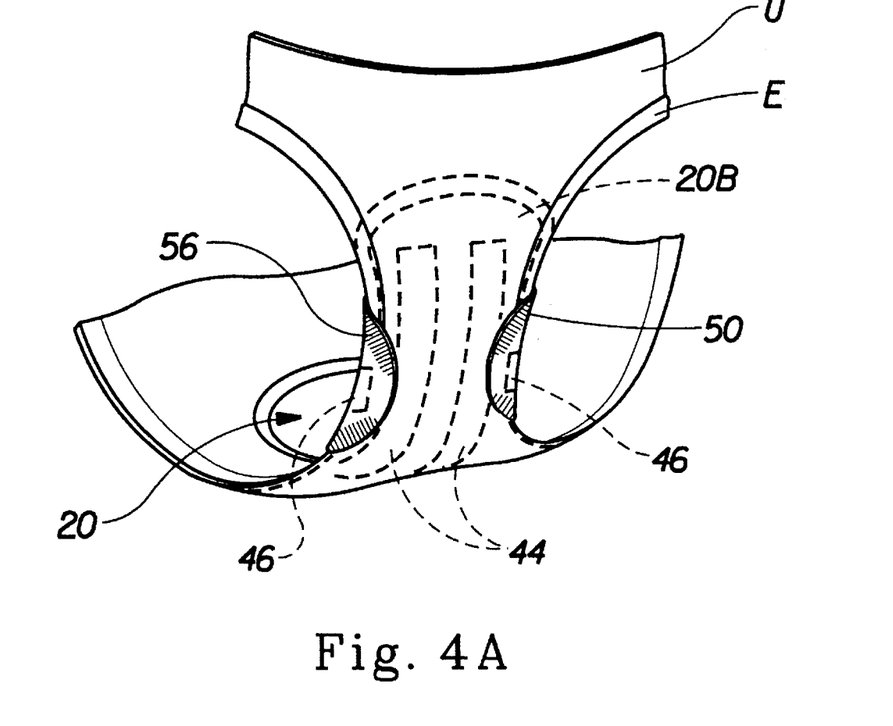
FIG. 4A is a perspective view of a portion of a panty with the sanitary napkin of the present invention in place with the side wrapping elements affixed to the underside of the wearer's panties.

The sanitary napkin 20 of the present invention is used by removing any release liner and thereafter placing the sanitary napkin 20 in a panty as shown in FIG. 4 so that the adhesive (or other fastener) 44 contacts the panty and maintains the sanitary napkin in position within the panty during use. The side wrapping elements 50 automatically wrap around the sides of the wearer's panties by the simple action of the wearer pulling up her panties. The side wrapping elements 50 then assume an in-use position, one non-limiting example of which is shown in FIG. 4. FIG. 4A shows that the side wrapping elements 50 can also attach to the underside of the wearer's panty crotch when the sanitary napkin is provided with fasteners that extend into the side wrapping elements 50, such as central lateral extensions 46. This can happen automatically when the wearer's thighs press the side wrapping elements 50 against the underside of the panty crotch, especially when the wearer's thighs are relatively large.

Figure 5:
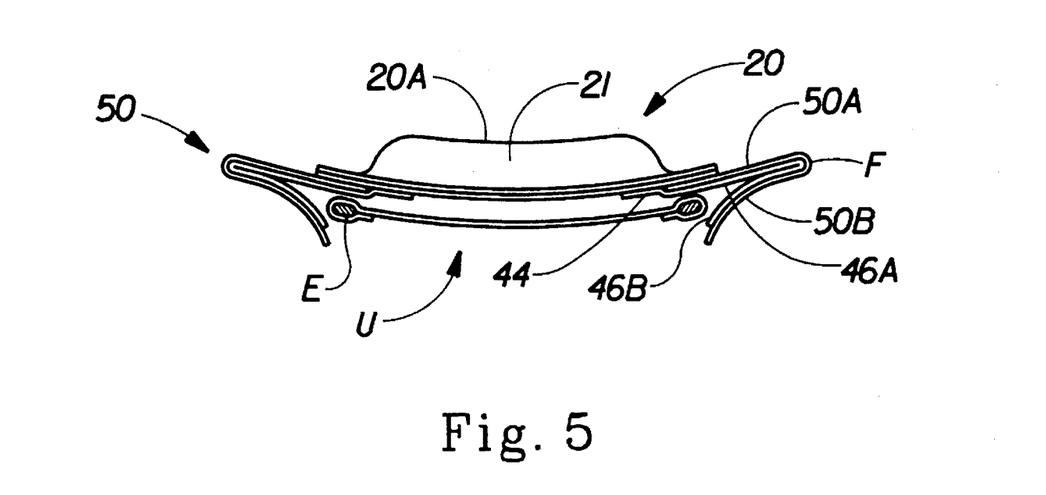
FIG. 5 is a schematic side view showing one way in which the side wrapping elements of the sanitary napkin might fold around and pinch the edge of a wearer's panties when the adhesive fastener on the undergarment-facing side extends out onto the side wrapping elements.

FIG. 5 shows a phenomena that may occur when the sanitary napkin is provided with side wrapping elements that have fasteners with central lateral extensions 46. The side wrapping elements 50 are shown as folding around a side edge E of a crotch portion of a wearer's undergarment, U, about a longitudinally-oriented fold line F. It has been found that the central lateral extensions 46 can be of such a size and configuration that when the sanitary napkin is worn in narrow panty crotches, the fold line F divides the central extensions 46 into two portions comprising a first portion 46A and a second portion 46B. In such cases, the fold line is disposed far enough outboard of the side edge of the crotch portion of said undergarment so that a portion of said side wrapping element 50 comprising a first and second portions 50A and 50B, respectively, of the side wrapping element 50 and the adhesive portions 46A and 46B thereon overlap and adhere to each other outboard of the side edge of said undergarment so that the side wrapping element forms a structure which can "grasp" or "pinch" the longitudinal edge of the panty crotch. This not only assists in maintaining the side wrapping elements 50 around the panty crotch when the panties are in place against the wearer's body, but also maintains the side wrapping elements 50 in position when the wearer pulls her panties down to check the sanitary napkin.

The operation of the side wrapping elements 50 is distinguishable in several aspects from that of conventional side flaps. First, placing a sanitary napkin having conventional flaps in a pair of panties and pulling up the panties will not consistently provide the automatic sustained wraparound feature of the present invention. There are several reasons for this. Conventional flaps are not provided with resistance to bending and crumpling so that they will tend to crumple in use, particularly when the wearer's thighs exert compressive forces on the flaps. Conventional flaps are also not provided with zones of extensibility, so they will generally not wrap around and conform to the panties. In those cases where conventional flaps do wrap around the panties, since conventional flaps do not have zones of extensibility they will not consistently stay wrapped. Second, conventionally-sized flaps will have excess flap material that hangs down underneath the panties during wear. This material can move around excessively underneath the panties and be uncomfortable for the wearer. The side wrapping elements of the present invention, on the other hand, have a span that is ideally just wide enough to wrap around the elastic-containing edges of the panties, but no wider, avoiding the problems associated with excess flap material.

2. Alternative Embodiments.

Numerous alternative embodiments of the present invention are possible. For example, the side wrapping elements are preferably mirror images of each other, and are symmetrical about the longitudinal centerline. However, it should be understood that the shape and location of the side wrapping elements described herein are those of a preferred embodiment, and other embodiments are also possible. For example, while the side wrapping elements 50 are shown as extending from each longitudinal edge of the main body portion, there may only be one side wrapping element extending from one of the edges of the main body portion. Further, the side wrapping elements 50 may be offset along the longitudinal centerline more towards one end edge of the main body portion than the other.

The terms "panty liner" or "pantiliner" refer to absorbent articles that are less bulky than sanitary napkins which are generally worn by women between their menstrual periods. Suitable absorbent articles in the form of pantiliners that can be provided with the side wrapping elements described herein are disclosed in U.S. Pat. No. 4,738,676 entitled "Pantiliner" issued to Osborn on Apr. 19, 1988.

The term "incontinence article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinent articles that can be provided with the side wrapping elements described herein are disclosed in U.S. Pat. No. 5,300,054 issued to Feist, et al. on Apr. 5, 1994 and U.S. Pat. No. 5,304,161 issued to Noel, et al. Apr. 19, 1994.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

3. Test Methods

The side wrapping elements 30 should provide sufficient bending and crumpling resistance so that they will fold rather than crumple in use and automatically wrap the edges of the wearer's panties. Bending and crumpling resistance is measured by the Flexure Bending Test.

FLEXURE BENDING TEST

The Flexure Bending Test is performed on samples that have been conditioned by leaving them in a room at 50% relative humidity and at 73° F. for a period of two hours prior to the test.

Figure 6:
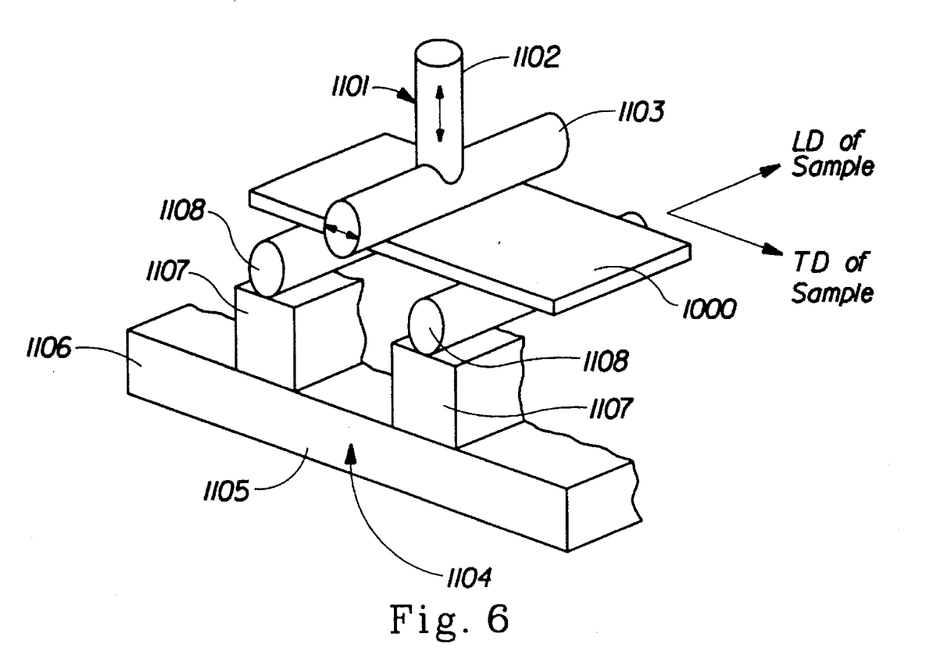
FIG. 6 is a schematic perspective view of the Flexure Bending Test apparatus.

The flexure bending test uses an INSTRON Model 4502 tensile and compression testing machine, which is available from Instron Corporation of Canton, Mass. The test also uses a special displacement "T-rod" and a special test sample holder. As shown in FIG. 6, the "T-rod" 1101 comprises a pair of ¼ inch (6.35 mm) diameter metal rods perpendicularly mounted together. The drive rod 1102 (the longer of the rods) is about 125 mm (about 5.25 inches) long and the push rod 1103 (the shorter of the rods) is about 75 mm (about 3 inches) long. Preferably, the end of the drive rod 1102 is tapered to fit the circumference of the push rod 1103 and the two are glued, welded and/or screwed to each other. The opposite end of the drive rod 1102 is mounted to the crosshead unit of the INSTRON machine. The test sample holder 1104 comprises a fixture base 1105 to position and support a pair of supporting rods 1108. The fixture base 1105 comprises a base 1105 and two rectangular supports 1107 mounted in parallel on the base 1106. The base 1106 and the supports 1107 are each preferably made of LEXAN (plexiglas) plate of about ⅜" to ½" (about 1 mm to 1.3 mm) thickness. A supporting rod 1108 of the same materials as the "T-bar" and about 150 mm (about 6 inches) long is mounted on each support 1107 of the fixture base 1105. The supporting rods 1108 are mounted so as to be spaced 16 mm apart, center-to-center. As shown in FIG. 6, the "Trod" 1101 is centered between the supporting rods 1108.

The INSTRON machine is set for a crosshead speed of 20 mm/min, a chart speed of 400 mm/min, and with full scale at 125 grams$_f$. The INSTRON machine is set up so that the crosshead unit will travel 6 mm down and back, with the chart provided by priming out the data from the test to follow the crosshead unit down and back.

The sample 1000 to be tested is taken from one of the side wrapping elements and placed so that the push rod 1103 is running parallel to the portion of the sample that was oriented in the longitudinal direction. The sample 1000 taken from the side wrapping elements should have a dimension between 50–75 mm in the longitudinal direction and a dimension in the transverse direction of a minimum of 16 mm, preferably 25 mm, or if neither is possible, any length available. Thus, it is more likely than not that in the actual test, the sample 1000 will be situated (differently from that shown in FIG. 6) wherein its longer dimension will be parallel to the push rod 1103. The garment-facing surface of the sample 1000 (typically the backsheet side) is placed toward the T-rod 1101.

The T-rod 1101 is "zeroed" on top of the sample 1000 with a preload of 1 gram$_f$. This takes out any bowing of the sample and insures good contact of the T-rod with the sample. Each sample is run through the 6 mm travel cycle twice, with a 30 second stop between cycles. A total of 10 samples are run.

Figure 7:
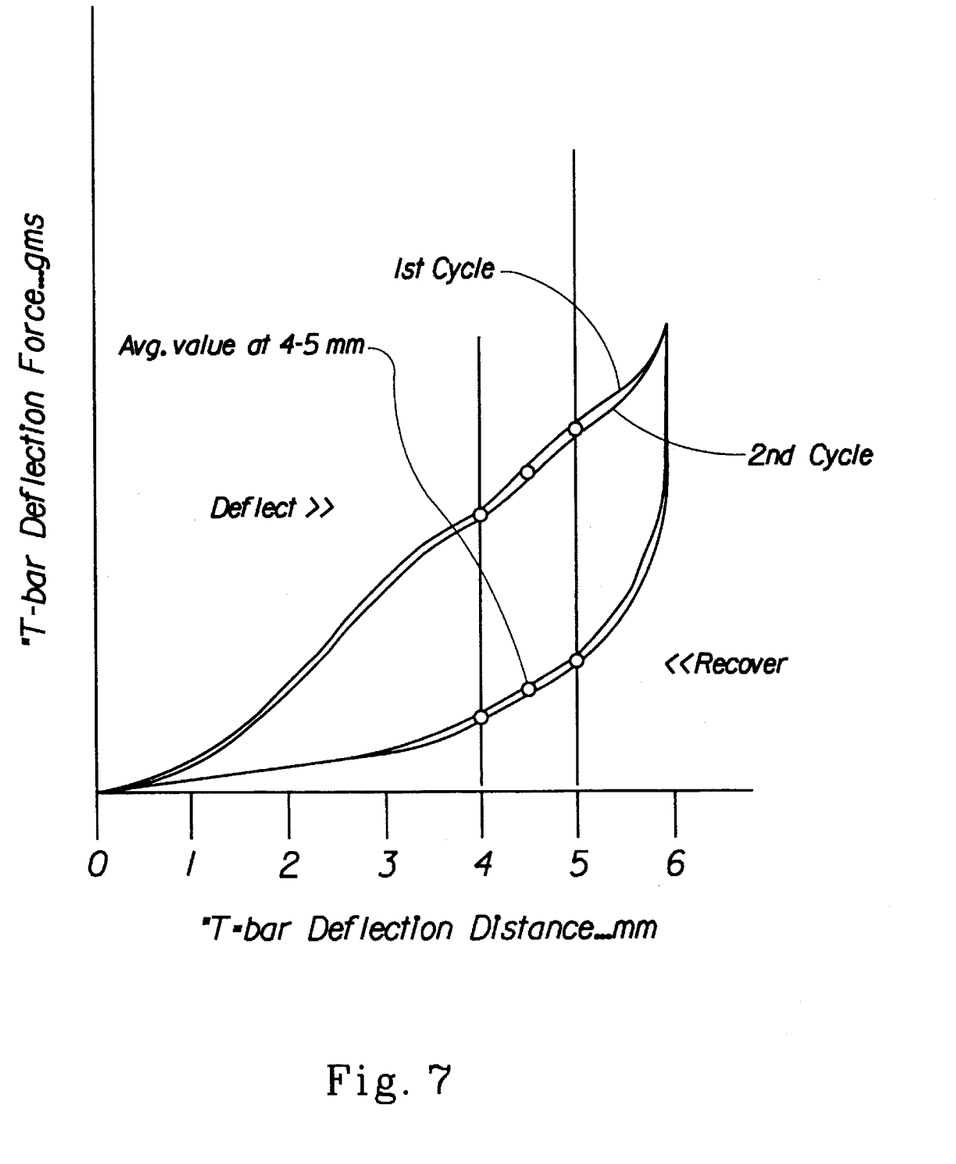
FIG. 7 is a graph showing some examples of the type of results that could be generated during the Flexure Bending Test procedure.

A graph of T-bar deflection force (grams$_f$) versus T-bar deflection distance (mm) will be generated. A representative run of a sample showing the two cycles is shown in FIG. 7. The deflection force at 4 mm and 5 mm, for each cycle, is determined on the recovery force curve. The recovery deflection force at 4 mm and 5 mm are averaged to calculate a cycle recovery deflection force. The average of both cycle recovery deflection forces for each sample determines the sample recovery deflection force. The bending flexure recovery force for the structure is the average of the value of the sample recovery deflection force for the 10 samples. The side wrapping elements should have a resistance to bending as measured in terms of bending flexure recovery force of between about 2 grams and about 50 grams, preferably between about 4 grams and about 30 grams, and more preferably between about 4 grams and about 15 grams.

While particular embodiments of the present invention have been illustrated and described, it would be obvious to those skilled in the art that various other changes and modifications can be made without departing from the spirit and scope of the invention.

What is claimed is:

1. An absorbent article for wearing in a wearer's undergarment that has a crotch region with a pair of side edges, said absorbent article having a longitudinal dimension extending in a longitudinal direction and a transverse dimension extending in a transverse direction, said absorbent article comprising:

a main body portion comprising an absorbent core, said main body portion having a body-facing side, a garment-facing side, and a pair of longitudinal side edges; and a pair of side wrapping elements for folding around the side edges of the wearer's undergarment, said side wrapping elements being joined to said main body portion and extending laterally outward beyond the longitudinal side edges of said main body portion a distance of less than one-half the width of said main body portion, to distal edges, said side wrapping elements having a transverse centerline, wherein at least one of said side wrapping element comprises at least one zone of extensibility and another region that is stiffer than said at least one zone of extensibility, said at least one zone of extensibility being extensible when folded around the side edges of an undergarment wherein said at least one zone of extensibility are capable of extending longitudinally greater than or equal to about 20 mm, said stiffer region has a resistance to bending of between about 2 grams and about 50 grams, and wherein said zones of extensibility are primarily extensible in the longitudinal direction.

2. The absorbent article of claim 1 wherein said zones of extensibility are extensible in a direction between the longitudinal direction and the transverse direction.

3. An absorbent article for wearing in a wearer's undergarment that has a crotch region with a pair of side edges, said absorbent article having a longitudinal dimension extending in a longitudinal direction and a transverse dimension extending in a transverse direction, said absorbent article comprising:

a main body portion comprising an absorbent core, said main body portion having a body-facing side, a garment-facing side, and a pair of longitudinal side edges; and a pair of side wrapping elements for folding around the side edges of the wearer's undergarment, said side wrapping elements being joined to said main body portion and extending laterally outward beyond the longitudinal side edges of said main body portion a distance of less than one-half the width of said main body portion, to distal edges, said side wrapping elements having a transverse centerline, wherein at least one of said side wrapping element comprises two zones of extensibility on opposite sides of said transverse centerline and an intermediate region positioned between said zones of extensibility, said intermediate region containing said transverse centerline and being stiffer than said zones of extensibility, said zones of extensibility being extensible when folded around the side edges of an undergarment wherein said zones of extensibility have portions therein which are capable of extending longitudinally greater than or equal to about 10 mm, the longitudinal distance between said portions is between about 20 mm and about 150 mm, and wherein said zones of extensibility are primarily extensible in the longitudinal direction.

4. The absorbent article of claim 3 wherein the longitudinal distance between said zones of extensibility is between about 30 mm and about 100 mm.

5. The absorbent article of claim 3 wherein said zones of extensibility are extensible in a direction between the longitudinal direction and the transverse direction.

6. The absorbent article of claim 3 wherein at least one zone of extensibility comprises a region of said side wrapping element which is provided with corrugations having fold lines therein.

7. The absorbent article of claim 3 wherein said zones of extensibility of said side wrapping elements are extensible in amounts greater than or equal to about 30% and less than or equal to about 80% under forces of less than about 200 grams, per inch.

8. The absorbent article of claim 7 wherein said zones of extensibility of said side wrapping elements are extensible between about 40% and 70% under such forces.

9. The absorbent article of claim 3 wherein said intermediate region has a proximal edge which forms a portion of the proximal edge of the side wrapping element and a distal edge which forms a portion of the distal edge of said side wrapping element, and said distal edge is shorter than said proximal edge.

10. The absorbent article of claim 3 wherein said zones of extensibility of said side wrapping element comprise laterally most inward points, said laterally most inward points being those points in said zones of extensibility that are located closest to said longitudinal centerline of said absorbent article, and said laterally most inward points define points on a predisposed fold line within said side wrapping element when the distance between said laterally most inward points on opposed side wrapping elements is greater than the width of the crotch region of the wearer's undergarment.

11. The absorbent article of claim 3 wherein said side wrapping elements are integral with said main body portion.

12. The absorbent article of claim 3 wherein said side wrapping elements comprise separate elements that are joined to the garment-facing side of said main body portion at a point of attachment located inward of the longitudinal side edges of said main body portion, and said side wrapping elements are unattached to said garment-facing side between point of attachment and the longitudinal side edge of said main body portion.

13. The absorbent article of claim 3 further comprising a pressure sensitive adhesive fastener in the form of two longitudinally oriented strips of adhesive disposed said garment-facing side of said main body portion on opposite sides of said longitudinal centerline, said strips of adhesive having central lateral extensions that extend into said intermediate regions of said side wrapping elements, wherein said central adhesive is spaced to secure said side wrapping elements to the wearer's undergarment at the elasticized side edges of the wearer's undergarment.

14. The absorbent article of claim 13 wherein said side wrapping element is configured to fold around a side edge of a crotch portion of a wearer's undergarment about a longitudinally-oriented fold line which divides said adhesive fastener in two portions comprising a first portion and a second portion and said fold line is disposed outboard of the side edge of the crotch portion of said undergarment so that a portion of said side wrapping element comprising said first and second portions of said side wrapping element overlap and adhere to each other outboard of the side edge of said undergarment.

* * * * *